United States Patent
Gerwick et al.

(10) Patent No.: US 9,073,884 B2
(45) Date of Patent: Jul. 7, 2015

(54) ANTI-INFLAMMATORY AND QUORUM SENSING INHIBITION COMPOUNDS AND METHODS OF MAKING AND USING THEM

(75) Inventors: William Gerwick, La Jolla, CA (US); Lena Gerwick, La Jolla, CA (US); Hyuakjae Choi, San Diego, CA (US); Francisco Villa, La Jolla, CA (US); Jennifer Smith, San Diego, CA (US); David C Rowley, Wakefield, RI (US)

(73) Assignees: The Regents of the University of California, Oakland, CA (US); University of Rhode Island Research Foundation, Kingston, RI (US)

( * ) Notice: Subject to any disclaimer, the term of this patent is extended or adjusted under 35 U.S.C. 154(b) by 297 days.

(21) Appl. No.: 13/696,583

(22) PCT Filed: Jun. 3, 2011

(86) PCT No.: PCT/US2011/039175
§ 371 (c)(1),
(2), (4) Date: Mar. 27, 2013

(87) PCT Pub. No.: WO2011/153502
PCT Pub. Date: Dec. 8, 2011

(65) Prior Publication Data
US 2014/0147481 A1 May 29, 2014

Related U.S. Application Data

(60) Provisional application No. 61/351,688, filed on Jun. 4, 2010.

(51) Int. Cl.
| | | |
|---|---|---|
| C07D 307/33 | (2006.01) |
| A61K 8/14 | (2006.01) |
| A61K 8/37 | (2006.01) |
| A61K 8/42 | (2006.01) |
| A61K 8/49 | (2006.01) |
| A61K 9/00 | (2006.01) |
| A61K 9/127 | (2006.01) |
| A61Q 11/00 | (2006.01) |
| C07C 57/54 | (2006.01) |
| A61L 27/54 | (2006.01) |
| A61L 29/16 | (2006.01) |
| A61L 31/16 | (2006.01) |
| A61K 8/69 | (2006.01) |
| C07C 57/52 | (2006.01) |
| C07C 69/732 | (2006.01) |
| C07C 233/15 | (2006.01) |

(52) U.S. Cl.
CPC ....... *C07D 307/33* (2013.01); *A61F 2310/0097* (2013.01); *A61K 8/14* (2013.01); *A61K 8/37* (2013.01); *A61K 8/42* (2013.01); *A61K 8/4973* (2013.01); *A61K 9/0019* (2013.01); *A61K 9/127* (2013.01); *A61Q 11/00* (2013.01); *C07C 57/54* (2013.01); *A61L 27/54* (2013.01); *A61L 29/16* (2013.01); *A61L 31/16* (2013.01); *A61L 2300/202* (2013.01); *A61L 2300/404* (2013.01); *A61L 2300/41* (2013.01); *A61K 8/69* (2013.01); *C07C 57/52* (2013.01); *C07C 69/732* (2013.01); *C07C 233/15* (2013.01)

(58) Field of Classification Search
CPC ..... C07C 57/54; C07C 69/732; C07D 307/33
See application file for complete search history.

(56) References Cited

U.S. PATENT DOCUMENTS 5,376,682 A * 12/1994 Naiki et al. ................... 514/473

FOREIGN PATENT DOCUMENTS

| WO | 9218614 | 10/1992 |
| WO | 9409766 | 5/1994 |

OTHER PUBLICATIONS

"Tert-butanol" Material Safety Data Sheet. Published Dec. 12, 1997.*
Werbel et al. "5-Phenyl-2,4-pentadienamides as Potential Antimalarial Agents" J. Med. Chem. 1967, 10 (3), 366-370.*
Winkler et al. "Food preservatives sodium sulfite and sorbic acid suppress mitogen-stimulated peripheral blood mononuclear cells" Food Chem. Tox. 2006, 44, 2003-2007.*
Weingart et al. "Direct binding of the quorum sensing regulator CepR of Burkholderia cenocepacia to two target promoters in vitro" Mol. Microbiol. 2005, 57 (2), 452-467.*
Baharlou, Simin, International Preliminary Report on Patentability, PCT/US2011/039175, Dec. 4, 2012.
Choi, Won Chul, International Search Report and Written Opinion, PCT/US2011/039175, Korean Intellectual Property Office, Feb. 28, 2012.

(Continued)

*Primary Examiner* — Sean Basquill
*Assistant Examiner* — Andrew S Rosenthal
(74) *Attorney, Agent, or Firm* — Gregory P. Einhorn; Greer, Burns & Crain, Ltd

(57) ABSTRACT

The invention provides novel compositions based on a structure designated as "Honaucin A", including Honaucin A variants and analogs, and pharmaceutical compositions, liposomes and nanoparticles comprising them, and methods of making and using them. In one embodiment, these Honaucin A compounds, and variants and analogs thereof are used to ameliorate (including to treat or prevent) inflammation. In one embodiment, these Honaucin A compounds, and variants and analogs thereof are used to ameliorate (including to treat or prevent) inflammation. In one embodiment, these Honaucin A compounds, and variants and analogs thereof are used as bacterial quorumsensing inhibitors. Accordingly, in alternative embodiments the compositions of the invention are used as anti-bacterial agents.

17 Claims, No Drawings

(56) References Cited

OTHER PUBLICATIONS

Goh et al., "Theoretical Study of Molecular Determinants Involved in Signal Binding to the TraR Protein of *Agrobacterium tumefaciens*," Molecules, 2005, 10, 1263-1271.

Weingart et al., "Direct binding of the quorum sensing regulator CepR of *Burkholderia cenocepacia* to two target promoters in vitro," Molecular Microbiology (2005) 57(2), pp. 452-467.

* cited by examiner

ANTI-INFLAMMATORY AND QUORUM SENSING INHIBITION COMPOUNDS AND METHODS OF MAKING AND USING THEM

This application is a national phase application claiming benefit of priority under 35 U.S.C. §371 to International (PCT) Patent Application serial number PCT/US2011/039175, filed Jun. 3, 2011, which claims benefit of priority to U.S. Provisional Patent Application Ser. No. 61/351,688, filed Jun. 4, 2010. The aforementioned applications are expressly incorporated herein by reference in their entirety and for all purposes.

GOVERNMENT RIGHTS

This invention was made with government support under grant TW006634 awarded by the National Institutes of Health (NIH). The government has certain rights in the invention.

TECHNICAL FIELD

This invention generally relates to biochemistry, cell biology and medicine. In alternative embodiments, the invention novel compositions based on a structure designated as "Honaucin A", including Honaucin A variants and analogs, and pharmaceutical compositions, liposomes and nanoparticles comprising them, and methods of making and using them. In one embodiment, these Honaucin A compounds, and variants and analogs thereof are used to ameliorate (including to treat or prevent) inflammation. In one embodiment these Honaucin A compounds, and variants and analogs thereof are used as bacterial quorumsensing inhibitors. Accordingly, in alternative embodiments the compositions of the invention are used as anti-bacterial agents.

BACKGROUND

Bacteria communicate with one another using chemical signal molecules that can be small hormone-like molecules, sometimes called autoinducers. The information supplied by these chemical signal molecules is critical for synchronizing the activities of large groups of bacterial cells. This chemical communication involves producing, releasing, detecting, and responding to the small hormone-like molecules, or autoinducers. This process is termed quorum sensing, and it allows bacteria to monitor the environment for other bacteria and to alter behavior on a population-wide scale in response to changes in the number and/or species present in a community. Most quorumsensing-controlled processes are beneficial when carried out simultaneously by a large number of cells. Thus, inhibition of quorumsensing can disrupt the health of a bacterial community, and if the bacteria are pathogenic or responsible for infection, inhibition of quorumsensing can have therapeutic, anti-bacterial value.

Members of the bacterial genus *Streptococcus* are responsible for causing a wide variety of infections in humans. Many *Streptococci* use quorum-sensing systems to regulate several physiological properties, including the ability to incorporate foreign DNA, tolerate acid, form biofilms, and become virulent. Biofilms, such as dental plaque, are dense aggregates of surface-adherent microorganisms embedded in an exopolysaccharide matrix.

SUMMARY

In alternative embodiments, the invention provides compositions based on a structure designated as "Honaucin A", including Honaucin A variants and analogs, and pharmaceutical compositions, liposomes and nanoparticles comprising them, and methods of making and using them. In one embodiment, these Honaucin A compounds, and variants and analogs thereof are used to ameliorate (including to treat or prevent) inflammation. In one embodiment, these Honaucin A compounds, and variants and analogs thereof are used as Bacterial quorumsensing inhibitors. Accordingly, in alternative embodiments the compositions of the invention are used as anti-bacterial agents.

In alternative embodiments, the invention provides compounds
(a) having a formula

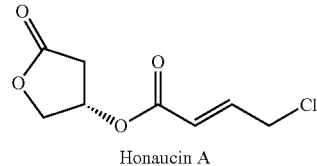 [SMILES: O=C(/C=C/CCl)O[C@@H]1COC(=O)C1]

Honaucin A or,
(b) derivatives or analogs of the compound of (a) comprising variations of chain length as compared to Honaucin A, variations of saturation level and halogenation on 4-Cl crotonic acid and ring size as compared to Honaucin A, and/or variations of position and/or chirality of substitutions on the lactone as compared to Honaucin A.

In alternative embodiments, the invention provides pharmaceutical compositions comprising a compound of the invention.

In alternative embodiments, the invention provides liposomes comprising a compound of the invention.

In alternative embodiments, the invention provides nanopartioles comprising a compound of the invention.

In alternative embodiments, the invention provides uses of Honaucin A, or a variant or analog thereof, for the manufacture of a medicament for the treatment, prevent or amelioration of a trauma, an infection, a disease or a condition associated with an infection or an inflammation; or as a bacterial quorumsensing inhibitor, wherein optionally the Honaucin A, or a variant or analog thereof comprises a compound of. In alternative embodiments of the use: the trauma, diseases or conditions treated or ameliorated by the medicament can comprise an inflammatory component; or the trauma, diseases or conditions treated or ameliorated by the medicament can be an autoimmune disease; or, the trauma can be a surgical trauma; or, the medicament treats or ameliorates a bacterial infection or acts as a bacterial quorumsensing inhibitor.

In alternative embodiments, the invention provides methods for treating, preventing or ameliorating an infection, or trauma, or disease or condition associated with inflammation, infection or trauma, comprising administering to an individual in need thereof a composition of the invention, a pharmaceutical composition of the invention, or the liposome of the invention, or the nanoparticle of the invention. In alternative embodiments of the methods: the diseases or conditions treated or ameliorated by the medicament comprise an inflammatory component; the diseases or conditions treated or ameliorated by the medicament is an autoimmune disease; or, the medicament treats or ameliorates inflammation caused by a surgical trauma.

In alternative embodiments, the invention provides methods for down-regulating IL-1, IL-6, TNF-alpha and/or iNOS at the transcriptional and/or translational level, comprising administering to a cell or a tissue a composition of the invention, a pharmaceutical composition of the invention, or the liposome of the invention, or the nanoparticle of the invention.

In alternative embodiments, the invention provides methods for down-regulating IL-1, IL-6 TNF-alpha and/or iNOS at the transcriptional and/or translational level, comprising administering to an individual in need thereof a composition of the invention, a pharmaceutical composition of the invention, or the liposome of the invention, or the nanoparticle of the invention.

In alternative embodiments, the invention provides antibiofilm reagents or compositions comprising a composition of the invention, a pharmaceutical composition of the invention, or the liposome of the invention, or the nanoparticle of the invention.

In alternative embodiments, the invention provides methods of inhibiting a biofilm in administering a composition of the invention, a pharmaceutical composition of the invention, or the liposome of the invention, or the nanoparticle of the invention, wherein optionally the biofilm is dental plaque.

In alternative embodiments, the invention provides methods of inhibiting a biofilm in an individual comprising administering to an individual in need thereof a composition of the invention, a pharmaceutical composition of the invention, or the liposome of the invention, or the nanoparticle of the invention, wherein optionally the biofilm is dental plaque.

In alternative embodiments, the invention provides antibacterial compositions comprising a composition of the invention, a pharmaceutical composition of the invention, or the liposome of the invention, or the nanoparticle of the invention, wherein optionally the anti-bacterial composition is formulated as a solution (e.g., a mouthwash), a powder, a tablet, a capsule, an aerosol, a gel or a liquid.

In alternative embodiments, the invention provides anti *Streptococcus* agents comprising a composition of the invention, a pharmaceutical composition of the invention, or the liposome of the invention, or the nanoparticle of the invention; wherein optionally the agent comprises or is formulated as a solution, (e.g., a mouthwash), a powder, a tablet, a capsule, an aerosol, a gel or a liquid.

The details of one or more embodiments of the invention are set forth in the accompanying drawings and the description below. Other features, objects, and advantages of the invention will be apparent from the description and drawings, and from the claims.

All publications, patents, patent applications, GenBank sequences and ATCC deposits, cited herein are hereby expressly incorporated by reference for all purposes.

DETAILED DESCRIPTION

In alternative embodiments, the invention novel compositions based on a structure designated as "Honaucin A", including Honaucin A variants and analogs, and pharmaceutical compositions, liposomes and nanoparticles comprising them, and methods of making and using them. In one embodiment, these Honaucin A compounds, and variants and analogs thereof are used to ameliorate (including to treat or prevent) inflammation. In one embodiment, these Honaucin A compounds, and variants and analogs thereof are used as bacterial quorumsensing inhibitors. Accordingly, in alternative embodiments the compositions of the invention are used as anti-bacterial agents.

In alternative embodiments, Honaucin A analogs and derivatives of the invention comprise variations of chain length as compared to Honaucin A, variations of saturation level and halogenation on 4-Cl crotonic acid and ring size as compared to Honaucin A, and variations of position and chirality of substitutions on the lactone as compared to Honaucin A.

The invention is not limited by any specific mechanism of action. In alternative embodiments, compounds of the invention can down regulate IL-1, IL-6, TNF-alpha and/or iNOS at the transcriptional and/or translational level. In alternative embodiments, compounds of the invention can inhibit quorum sensing; this can be measured using quorum sensing assays measuring either AI-1 or AI-2 activity.

Pharmaceutical Compositions

The invention provides pharmaceutical compositions comprising a structure designated as "Honaucin A", including Honaucin A variants and analogs, and methods for making and using these pharmaceutical compositions. e.g., in the manufacture of medicaments for ameliorating inflammation and diseases having an inflammatory component or symptom or sequelae comprising an inflammatory component; and as bacterial quorumsensing inhibitors; and other conditions and diseases as described herein.

The Honaucin A and Honaucin A variants and analogs of the invention of the invention, and the pharmaceutical compositions comprising them, can be combined with, or used in conjunction with, any anti-inflammatory agent or antibacterial agent, e.g., an antibiotic.

In alternative embodiments, the Honaucin A and Honaucin A variants and analogs of the invention of the invention are formulated with a pharmaceutically acceptable carrier. In alternative embodiments, the pharmaceutical compositions of the invention can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents of the invention can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of lipopeptides and analogs of the invention include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations of this invention can be prepared according to any method known to the art for the manufacture of pharmaceuticals. Such drugs can contain sweetening agents, flavoring agents, coloring agents and preserving agents. A formulation can be admixtured with non-toxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, e.g., push-fit capsules made of gelatin, as well as soft, sealed capsules made of gelatin, and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., Honaucin A and Honaucin A variants and analogs of the invention) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid, (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration of the hydrophobic active agents of the invention, including the somocystinamide A and analogs of the invention. Oil-based suspensions can be formulated by suspending an active agent (e.g., a somocystinamide A analog of the invention) in a vegetable oil, such as arachis oil, olive oil, sesame oil or coconut oil, or in a mineral oil such as liquid paraffin; or a mixture of these. See e.g., U.S. Pat. No. 5,716, 928 describing using essential oils or essential oil components for increasing bioavailability and reducing inter- and intra-individual variability of orally administered hydrophobic pharmaceutical compounds (see also U.S. Pat. No. 5,858, 401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997), J. Pharmacol Exp. Ther. 281:93-102. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such, as polyoxyethylene sorbitan mono-oleate. The emulsion can also contain sweetening agents and flavoring agents, as in the formulation of syrups and elixirs. Such formulations can also contain a demulcent a preservative, or a coloring agent.

In practicing this invention, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing this invention, the pharmaceutical compounds can be delivered by transdermally, by a topical route, formulated as applicator sticks, solutions, suspensions, emulsions, gels, creams, ointments, pastes, jellies, paints, powders, and aerosols.

In practicing this invention, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol, 49:669-674.

In practicing this invention, the pharmaceutical compounds can be parenterally administered such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilisation techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium, lactate and the like. The concentration of active agent, in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation, can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations of the invention can be lyophilized. The invention provides a stable lyophilized formulation comprising a composition of the invention, which can be made by lyophilizing a solution comprising a pharmaceutical of the invention and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations of the invention, can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations of the invention can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions of the invention are administered in an amount sufficient to treat, prevent and/or ameliorate inflammation or an infection. The amount, of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of Honaucin A or Honaucin A variants and analogs of the invention thereof is in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods of the invention can further comprise co-administration with other drugs or pharmaceuticals, e.g., compositions for infection, fever, pain, and related symptoms or conditions. For example, the methods and/or compositions and formulations of the invention can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

The invention also provides nanoparticles and liposomal membranes which target specific molecules, including biologic molecules, such as polypeptide, including cell surface polypeptides. Thus, in alternative embodiments, the invention, provides nanoparticles and liposomal membranes targeting areas of inflammation; e.g., an organ that is chronically inflamed due to a disease or condition, e.g., an autoimmune disease.

In alternative embodiments, the invention provides nanoparticles and liposomal membranes comprising molecules, e.g., peptides or antibodies, that selectively target diseased, infected, dysfunctional and/or cancer (tumor) cell receptors. In alternative embodiments, the invention provides nanoparticles and liposomal membranes using IL-11 receptor and/or the GRP78 receptor to targeted receptors on cells, e.g., on tumor cells. See, e.g., U.S. patent application publication no. 20060239968.

Thus, in one aspect, the compositions of the invention are specifically targeted for tumor-associated or disease- or infection-associated, neovasculature.

The invention also provides nanocells to allow the sequential delivery of two different therapeutic agents with different modes of action or different pharmacokinetics, at least one of which comprises a composition of this invention. A nanocell is formed by encapsulating a nanocore with a first agent inside a lipid vesicle containing a second agent; see. e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as cancer, inflammatory diseases such as asthma, autoimmune diseases such as rheumatoid arthritis or infectious diseases. For example, in treating the inflammatory component subsequent to a cancer treatment, a traditional antineoplastic agent is contained in the outer lipid vesicle of the nanocell and an anti-inflammatory agent of this invention is loaded into the nanocore.

The invention also provides multilayered liposomes, e.g., for transdermal absorption, e.g., as described in Park, et al., U.S. Pat. Pub. No. 20070082042. The muitilayered liposomes can be prepared using a mixture of oil-phase components comprising squalane, sterols, ceramides, neutral lipids or oils, fatty acids and lecithins, to about 200 to 5000 nm in particle size, to entrap a composition of this invention.

A multilayered liposome of the invention may further include an antiseptic, an antioxidant, a stabiliser, a thickener, and the like to improve stability. Synthetic and natural antiseptics can be used, e.g., in an amount of 0.01% to 20%. Antioxidants can be used, e.g., BHT, erysorbate, tocopherol, astaxanthin vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, polyacrylamide or polyvinylpyrollidone and polyvinylalcohol, and copolymers thereof or cross-linked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution, in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

The invention also provides nanoparticles to deliver a composition, of the invention as a drug-containing nanoparticles (e.g., a secondary nanoparticle), as described, e.g., in U.S. Pat. Pub. No. 20070077286. In one embodiment, the invention provides nanoparticles comprising a fat-soluble drug of this invention or a fat-solubilized water-soluble drug to act with a bivalent or trivalent metal salt.

Kits and Libraries

The invention, provides kits comprising compositions and methods of the invention, including instructions regarding the methods of the invention, or any combination thereof. As such, kits, cells, vectors and the like are provided herein.

The invention will be further described with reference to the following examples; however, it is to be understood that the invention is not limited to such examples.

EXAMPLES

Example 1

Identifying Compounds of the Invention as Anti-Inflammatory Agents and Demonstrating their Efficacy This example provides data demonstrating Honaucin A and Honaucin A variants and analogs of the invention are effective anti-inflammatory agents.

Honaucin A has been isolated and complete structure determined. The in vitro anti-inflammatory activity of the compound has been assayed in the Griess assay (see e.g., Tsikas, et al. (1998) *J. Chromatogr. B* 715:441-444) using RAW 264.7 cells, and follow up qRTPCR has been done to verify the results from the Griess assay. Honaucin A has also been tested in the *vibrio harveyi* assay and the *Escherichia coli* JB525 (*E. coli* MT102 harboring the gfp plasmid pJBA132) assay and is showing good inhibition of AI-1 and AI-2 mediated quorum sensing (see e.g., Waters, et al., (2005) Annu. Rev. Cell Dev. Biol. 21:319-46; Surette, et al. (1999) Proc. Natl. Acad. Sci. USA 96:1639-44).

Example 2

Nanoparticles of the Invention

The invention provides nanoparticles and liposomal membranes comprising the Honaucin A and Honaucin A variants and analogs of the invention of the invention as, e.g., pharmaceutical compositions comprising them.

In one aspect, Honaucin A and Honaucin A variants and analogs of the invention of the invention are incorporated into liposomal membranes to produce stable nanoparticles of about 100 nM in size. The invention also provides nanoparticles of any size, e.g., from anywhere between about 10 to 1000 nM, 50 to 500 nM, or 75 to 250 nM in size.

Honaucin A and Honaucin A variants and analogs of the invention can be incorporated into liposomal membranes to produce stable nanoparticles of between about 10 to 1000 nM, 50 to 500 nM, or 75 to 250 nM in size, or about 100 nM in size. The invention also provides targeted nanoparticles incorporating Honaucin A and Honaucin A variants and analogs of the invention.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating or ameliorating an infection or trauma, or disease or condition associated with inflammation, infection or trauma, comprising administering to an individual in need thereof a compound
   (a) having a formula selected from the group consisting of:

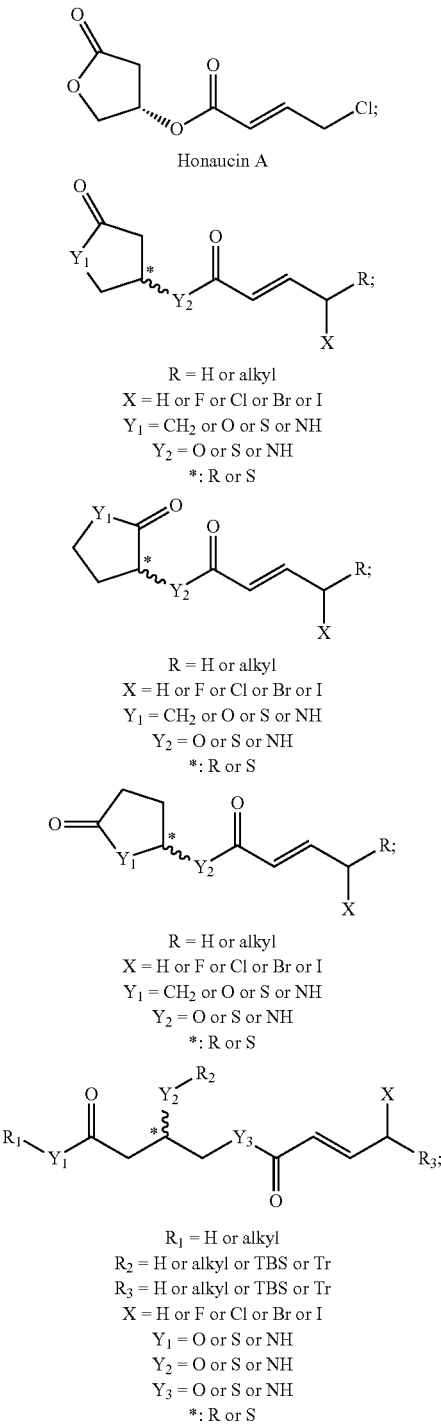

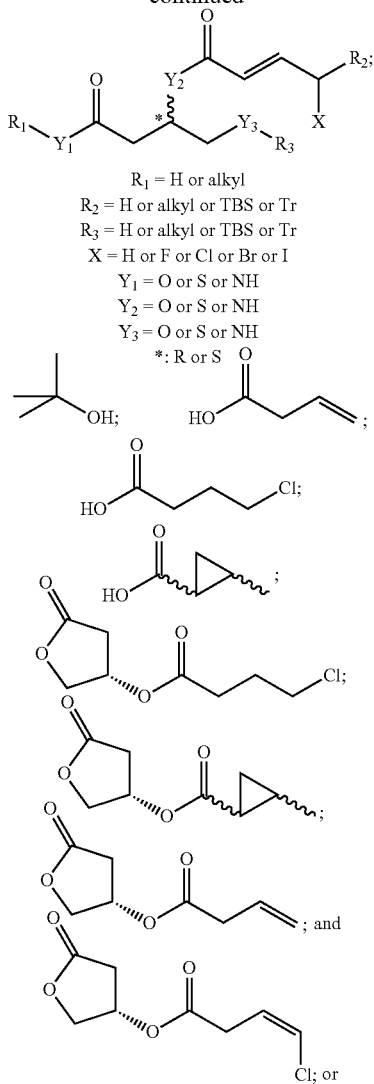

(b) derivatives or analogs of the compounds of (a) comprising variations of saturation level and halogenation of the 4-chloro crotonic acid functional group.

2. The method of claim 1, wherein the disease or condition treated or ameliorated comprises an inflammatory component.

3. The method of claim 1, wherein:
   (a) the derivatives or analogs optionally comprise variations of chain length or chain saturation comprising alkene or alkyne moieties;
   (b) the variations of chain length or chain saturation comprise a chain moiety —COO—($C_n$)—Cl, where the integer n can be 2, 3, 4, 5, 6, 7, 8, 9, 10, 11, 12, 13, 14 or 15 or more;
   (c) the derivatives or analogs comprise variations of halogenation, or a substitution of a bromine, an iodine, an astatine, or a fluorine for the chlorine group;
   (d) the compound is a polyhalogenated compound, or a polyhalogenated compound further comprising a second or third or an additional halogen moiety; or
   (e) the ring and/or chain are substituted with a hydrogen, halo, hydroxy (—OH), phenoxy, thiol (—SH), cyano (—CN), formyl (—CHO), alkyl, haloalkyl, alkene, alkenyl, alkynyl, heteroalkyl, heteroalkenyl, heteroalkynyl, aryl, substituted aryl, amino, nitro (—$NO_2$), alkoxy, haloalkoxy, thioalkoxy, alkanoyl, haloalkanoyl and/or carbonyloxy group.

4. The method of claim 1, wherein any one, several or all of the hydrogen groups are independently substituted with a fluorine or a deuterium.

5. The method of claim 1, wherein the derivatives or analogs comprise have a six membered ring with or without an oxygen, or a phenolic ring.

6. The method of claim 1, one, several or all of the oxygen groups are independently substituted with a sulfur moiety.

7. The method of claim 1, wherein the compound is formulated as a pharmaceutical composition.

8. The method of claim 1, wherein the compound is formulated as a liposome.

9. The method of claim 1, wherein the compound is formulated as a nanoparticle.

10. The method of claim 1, wherein the administered compound has the formula:

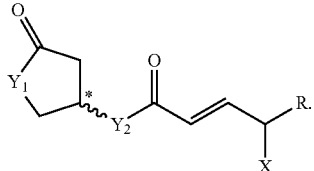

R = H or alkyl
X = H or F or Cl or Br or I
$Y_1$ = $CH_2$ or O or S or NH
$Y_2$ = O or S or NH
*: R or S 11. The method of claim 10, wherein the administered compound is Honaucin A.

12. The method of claim 1, wherein the method comprises treating or ameliorating an infection.

13. The method of claim 1, wherein the method comprises treating or ameliorating a trauma.

14. The method of claim 1, wherein the method comprises treating or ameliorating a disease or condition associated with inflammation.

15. The method of claim 1, wherein the method comprises treating or ameliorating a disease or condition associated with a trauma.

16. The method of claim 1, wherein the method comprises treating or ameliorating an autoimmune disease.

17. The method of claim 1, wherein the method comprises treating or ameliorating inflammation caused by a surgical trauma.

* * * * *